United States Patent [19]
Maurin

[11] Patent Number: 5,888,478
[45] Date of Patent: Mar. 30, 1999

[54] TRANSPARENT PRESSURIZED DEVICE WITH FOAMING COMPOSITION INCLUDING NONIONIC AND AMPHOTERIC SURFACTANTS

[75] Inventor: Véronique Maurin, Paris, France

[73] Assignee: L'Oreal, Paris, France

[21] Appl. No.: 808,416

[22] Filed: Feb. 28, 1997

[30] Foreign Application Priority Data

Mar. 1, 1996 [FR] France ................... 96 02628

[51] Int. Cl.⁶ ..................................................... A61K 7/00
[52] U.S. Cl. ........................... 424/45; 424/47; 424/400; 424/78.02; 424/78.03; 424/78.06; 424/78.07
[58] Field of Search .................... 424/45, 47, 73, 424/400, 401, 78.08, 78.02, 78.03, 78.06, 78.07

[56] References Cited

U.S. PATENT DOCUMENTS

| | | | |
|---|---|---|---|
| 5,156,833 | 10/1992 | Osugi et al. | 424/46 |
| 5,167,950 | 12/1992 | Lins | 424/47 |
| 5,354,510 | 10/1994 | Vanlerberghe et al. | 252/548 |
| 5,429,815 | 7/1995 | Faryniarz et al. | 424/47 |
| 5,464,874 | 11/1995 | Balzer | 574/777 |
| 5,648,069 | 7/1997 | Dillenburg et al. | 424/65 |
| 5,653,970 | 8/1997 | Vermeer | 424/70.24 |

FOREIGN PATENT DOCUMENTS

| | | |
|---|---|---|
| 6276 | 11/1967 | Australia . |
| 1002256 | 12/1986 | Canada . |
| 0194097 | 9/1986 | European Pat. Off. . |
| 0213827 | 3/1987 | European Pat. Off. . |
| 0304713 | 3/1989 | European Pat. Off. . |
| 0577506A1 | 1/1994 | European Pat. Off. . |
| 0586295A1 | 3/1994 | European Pat. Off. . |
| 0676188A2 | 10/1995 | European Pat. Off. . |
| WO 93/09761 | 5/1993 | WIPO . |
| WO 95/05796 | 3/1995 | WIPO . |

OTHER PUBLICATIONS

Patent Abstracts of Japan, vol. 12, No. 467 (C–550) [3314] Dec. 7, 1988, and English Derwent Abstract of JP 63185911.
Patent Abstracts of Japan, vol. 13, No. 339 (C–624) 36871 Jul. 31, 1989, and English Derwent Abstract of JP 01117817.
English Derwent Abstract of EP 304713 (89).
English Derwent Abstract of EP 586295 (94).

*Primary Examiner*—Neil S. Levy
*Attorney, Agent, or Firm*—Finnegan, Henderson, Farabow, Garrett & Dunner, L.L.P.

[57] ABSTRACT

New transparent pressurized devices including a very soft, foaming, stable, transparent cosmetic composition pressurized with a hydrocarbon gas, free from $C_1$–$C_3$ monohydric alcohols and including nonionic and amphoteric surfactants. Such compositions permit cleansing and removing make-up from the skin gently and effectively.

28 Claims, No Drawings

TRANSPARENT PRESSURIZED DEVICE WITH FOAMING COMPOSITION INCLUDING NONIONIC AND AMPHOTERIC SURFACTANTS

The invention relates to new pressurized devices including a composition, especially a cosmetic or dermatological composition and in particular a composition which is cleansing and which removes make-up.

The user expects that a composition for removing make-up will make it possible to remove all kinds of make-up products: lipstick, powder, eye shadow, foundation and the like, without damaging the skin and leaving it clean and soft. Cleansing the skin is very important for facial care. It must be as effective as possible because fatty residues such as the excess of sebum, the remainders of cosmetic products employed daily, especially make-up products and in particular the water-resistant "waterproof" products, accumulate in skin folds and can block the pores of the skin and result in the appearance of pimples. The usual make-up removers are generally in the form of a gel, a lotion or a cream. However, the market awaits new forms of products, which are simultaneously more aesthetic and possibly entertaining. To meet this expectation, new make-up removers and cleansers for the skin have appeared, in the form of transparent pressurized devices containing a foaming, single-phase, transparent, cleansing and make-up remover composition.

Single-phase and stable, transparent, foaming, compositions for topical application which are packaged in pressurized bottles are known in particular from U.S. Pat. No. 3,719,752. These compositions include a surfactant and a propellent gas in a hydroalcoholic medium. The alcohol is preferably a $C_1$–$C_3$ monohydric alcohol. However, the use of alcohol, and in particular of ethanol, in such compositions involves a hazard linked with flammability. Consequently, attempts have been made to avoid the use of $C_1$–$C_3$ monohydric alcohol in facial cleansing compositions.

Furthermore, International Application No. WO95/05796 describes a pressurized device including a fluid, single-phase composition free from monohydric alcohol, consisting of a hydrocarbon propellent gas and of an aqueous concentrate including α-olefinsulphonate salts, betaines and alkylpolyglucosides, which is contained in a transparent bottle. However, this device is not devoid of disadvantages. The composition which it contains is not stable with time; in particular a halo of aggregates in suspension in the composition is seen to appear on storage. Since the pressurized bottle is transparent, such an instability is not acceptable to the consumer.

European Patent Application No. EP-676188 discloses a similar device, including a fluid, single-phase composition free from monohydric alcohol, consisting of a propellent gas and of an aqueous concentrate. The propellent gas includes a mixture of dimethyl ether and of hydrocarbon gas. The aqueous concentrate includes surfactants and, in addition, a coupling agent. It is known, furthermore, that dimethyl ether is a flammable gas with a very low flash point. Its use therefore increases the hazards linked with pressurized devices, both in the case of the production site and in the case of the user of this device.

Canadian Patent No. CA-1002256 discloses a uniform, transparent pressurized system which can be employed for dispensing transparent aqueous cosmetic products, including products for removing make-up. The use of a triethanolamine salt of an acyl lactylic acid as a surfactant allows a system to be obtained in which the propellent gas is completely dissolved in the aqueous phase.

U.S. Pat. No. 3,840,465 discloses a transparent pressurized system including an alcohol-free, foaming, transparent composition. This composition includes an aqueous solution of a foaming surfactant, which is generally anionic, in which a liquid propellant is dispersed by virtue of a second surfactant which is soluble in the propellant and insoluble in water.

The compositions described in all these documents and employed for cleansing the skin consist essentially of anionic surfactants which destroy the hydro-lipid film of the skin and leave the skin clean but rough.

Thus, it is with great surprise that the inventor has discovered new devices including a very mild, foaming, stable, transparent cosmetic composition pressurized with a hydrocarbon gas, free from $C_1$–$C_3$ monohydric alcohols, based on nonionic surfactants, and optionally including one or a number of amphoteric surfactants.

The subject-matter of the invention is a pressurized device comprising (I) a pressurized bottle provided with a dispensing head; and (ii) a single-phase transparent composition contained in the bottle comprising:
A—0.5 to 10% of a propellent gas; and
B≦90 to 99.5% of an aqueous composition, this device being suitable for dispensing a foam when the dispensing head is activated, characterized in that the composition B includes a mixture of surfactants which are selected from nonionic surfactants and amphoteric surfactants.

When the push button forming part of the dispensing head is activated, the compositions of the invention are dispensed in the form of a creamy foam which cleanses the skin without attacking it. The absence of anionic and cationic surfactants in the compositions dispensed by this device has the effect of obtaining a foam of a product that is extremely mild for the skin and for the mucosae (lips, inside of the eyelids). This allows the composition to be employed for cleansing and removing make-up from the face, in particular for removing eye make-up.

The pressurized bottles employed in the invention are preferably transparent. Such bottles are well known to a person skilled in the art and commonly employed as shown, for example, in International Patent Application No. WO95/05796, the disclosure of which is incorporated herein by reference. They exploit the surprising character of the invention, i.e., a transparent emulsion which has a fluidity comparable to that of water as seen through the bottle, the emulsion being restored into the form of a creamy foam through the dispensing means, and not in the form of a spray as is a priori expected therefrom. Any means for dispensing from an aerosol bottle which is known to a person skilled in the art can be employed. A bottle and a means of dispensing that can be employed in the present invention are shown, for example, in French Patent Application No. FR-95-12788, the disclosure of which is incorporated herein by reference.

The word "transparent" means that through the bottle containing the composition it is possible to discern the printed characters on a newspaper page placed behind this bottle. This term also means that a 1 0-cm thick sample of the composition has a maximum light transmission of at least 4% at any wavelength of from 200 nm to 800 nm.

More particularly, the subject-matter of the invention is a pressurized device as described above, characterized in that the aqueous composition B includes:

(a) at least one nonionic emulsifying surfactant; and
(b) at least one nonionic thickening surfactant.

The aqueous composition B preferably includes 1 to 25% by weight of at least one nonionic emulsifying surfactant.

Advantageously, the aqueous composition B includes 1 to 30% of at least one nonionic thickening surfactant.

The composition of B is preferably adjusted, and in particular the choice and the percentage of the thickener(s), in such a way that this composition B has a Brookfield viscosity of from 5 to 200 mPa s and preferably from 10 to 150 mPa s.

Any propellent gases known for such applications may be employed in the devices according to the invention. There may be mentioned, in particular, hydrocarbon gases like, for example, propane, n-butane, isobutane and mixtures thereof, and fluorinated gases like, for example, chlorodifluoromethane, dichlorodifluoromethane, difluoroethane, chlorodifluoroethane, dichlorotetrafluoroethane and the like, and mixtures thereof. Nitrogen, air and carbon dioxide and their mixtures can also be employed as propellent gases in the present invention. Hydrocarbon gases containing from 2 to 6 carbon atoms are preferably employed in the present invention. Among the compositions of the invention preference is given to those containing from 1.5 to 4%, by weight relative to the total weight of the composition, of propellent gas.

The emulsifying surfactants which can be employed in the present invention are preferably selected from those which have an HLB balance of from 12 to 18. The HLB balance (hydrophilic-lipophilic balance) of an emulsifier is calculated according to the following formula:

HLB=(100−L)/5 in which L denotes the percentage by weight of the lipophilic group relative to the weight of the entire molecule.

These surfactants are preferably selected from the products of addition of 1 to 200 moles of ethylene oxide or of propylene oxide to partial esters of polyols containing 2 to 16 carbon atoms and of fatty acids containing 12 to 22 carbon atoms. Products such as described above which have a degree of esterification lower than or equal to 2 are advantageously chosen.

The nonionic thickening surfactants which can be employed in the present invention are preferably selected from:

(a) the $C_1$–$C_6$ alkanolamides of carboxylic $C_8$–$C_{22}$ alkyl ether acids;

(b) the products of addition of 10 to 300 moles of ethylene oxide or of propylene oxide to partial esters of polyols containing 2 to 16 carbon atoms and of fatty acids containing 12 to 22 carbon atoms. In this class of products, those which have a degree of esterification higher than or equal to 2 are preferably chosen;

(c) polyoxyethylenated and/or polyoxypropylenated and/or polyglycerolated $C_{12}$–$C_{22}$ fatty alcohols, (d) $C_{12}$–$C_{22}$ fatty esters of polyoxyethylene and/or of polyoxypropylene and/or of polyglycerol, (e) polyethylene glycol and/or polypropylene glycol block polymers.

The compositions according to the invention advantageously include at least two thickening surfactants, each belonging to two different classes, from the thickener classes (a) to (e) described above.

Preferably the $C_1$–$C_6$ alkanolamide of carboxylic $C_8$–$C_{22}$ alkyl ether acid products mentioned above correspond to formula (I):

in which R denotes an alkyl chain containing 8 to 30 carbon atoms, R' denotes an alkyl chain containing 1 to 6 carbon atoms, Y denotes an ethylenedlyl or 1,3-propylenediyl radical and n denotes an integer ranging from 0 to 100.

For example, R may be selected from stearyl, oleyl, ricinoleyl, linoleyl, lauryl, myristyl, capryl and palmityl radicals or from mixtures of $C_8$–$C_{22}$ alkyl radicals.

Among the partial esters of polyols which can be employed in the present invention there may be mentioned particularly those derived from glycol, glycerol and sugars like, for example, glucose, fructose, maltose, ribose, arabinose, xylose, lyxose, ribulose, xylulose, allose, altrose, mannose, gulose, galactose, sucrose or sorbitol.

The following products may be mentioned, for example, among the thickening surfactants which can be employed in the present invention: castor oil, monoethanolamides of carboxylic alkyl ($C_{13}$, $C_{15}$) ether acid (2 EO), the monoethanolamide of carboxylic ether acid (50 EO), oxyethylenated (200 EO) tallow mono- and diglycerides, oxyethylenated (82 EO) tallow mono- and diglycerides, oxyethylenated (78 EO) copra mono- and diglycerides, stearic and hydroxystearic acid triglycerides (40 EO), polyethylene glycol monostearate (100 EO), polyglycerolated (3.5 moles) dodecanediol alcohol and, more generally, the products described in French Patent No. FR-2091516, the disclosure of which is incorporated herein by reference, oxyethylenated (250 EO) 2-octyldodecanol, oxyethylenated (100 EO) stearyl alcohol, oxyethylenated (50 EO) oleyl alcohol, polyethylene glycol (50 EO) dioleate, oxyethylenated (200 EO) glycerol palmitate, oxyethylenated (160 EO) sorbitan triisostearate, oxyethylenated (200 EO) sorbitan triisostearate, polyethylene glycol (150 EO) stearate, oxyethylenated (120 EO) methylglucose dioleate, oxyethylenated (150 EO) pentaerythrityl tetrastearate, polyethylene glycol (55 EO) dioleate, polyethylene glycol (300 EO) undecylenate and polyethylene glycol (150 EO) distearate.

Among the polyoxyalkylenated polyol esters which can be employed as emulsifying surfactants mention may preferably be made of: oxyethylenated (7 EO) glycerol monoundecylenate, oxyethylenated (15 EO) glycerol monostearate, oxyethylenated (20 EO) glycerol monolaurate, oxyethylenated (20 EO) glycerol dilaurate, oxyethylenated (4 EO) diglycerol stearate, oxyethylenated (7 EO) glycerol cocoate, the pyrrolidonecarboxylate of oxyethylenated (25 EO) glycerol monoisostearate, oxyethylenated (20 EO) glycerol monostearate, oxyethylenated (30 EO) glycerol monostearate, oxyethylenated (4 EO) diglycerol stearate, oxyethylenated (30 EO) copra mono- and diglycerides, oxyethylenated (40 EO) sorbitan lanolate, oxyethylenated (20 EO) sorbitan monooleate, oxyethylenated (20 EO) sorbitan trioleate, oxyethylenated (20 EO) sorbitan monopalmitate, oxyethylenated (20 EO) sorbitan monostearate, oxyethylenated (20 EO) sorbitan monolaurate, oxyethylenated (20 EO) sorbitan undecylenate, oxyethylenated (18 EO) sorbitan undecylenate, oxyethylenated (6 EO) sorbitan hexastearate, oxyethylenated (44 EO) sorbitan monolaurate, oxyethylenated (30 EO) sorbitan tetraoleate, oxyethylenated (4 EO) sorbitan monostearate, oxyethylenated (40 EO) sorbitan oleate, oxyethylenated (4 EO) sorbitan monolaurate, oxyethylenated (10 EO) sorbitan monolaurate, oxyethylenated (40 EO) sorbitan tetraoleate, oxyethylenated (3 EO) butylglucoside cocoate, oxypropylenated (20 PO) methylglucoside distearate, oxyethylenated (20 EO) methylglucoside monolaurate, oxyethylenated (20 EO) methylglucose benzoate, oxyethylenated (1.4 EO) castor and sucrose triglyceride esters, oxyethylenated (2 EO) castor and sucrose triglyceride esters, oxyethylenated (20 EO) methylglucose sesquistearate, oxyethylenated (20 EO) methylglucose distearate, oxyethylenated (4 EO) butanediol monostearate, oxyethylenated (50 EO) polyethylene glycol monostearate, polyethylene glycol distearate, polyethylene glycol (8 EO) myristate, polyethylene glycol (8 EO) monostearate, polyethylene glycol (20 EO) monostearate, polyethylene glycol (6 EO) laurate, polyethylene glycol (8 EO) distearate, polyethylene glycol (8 EO) dilaurate, polyethylene glycol (8 EO) monooleate, tetraethylene glycol diheptanoate, polyethylene glycol (8 EO) dioleate, polypropylene glycol (26 EO) oleate, polyethylene glycol (30 EO) dipolyhydroxystearate (6 hydroxy), polyethylene glycol (40 EO) stearate and polyethylene glycol (8 EO) dilaurate.

All the products employed in the present invention are available commercially:

the $C_1$–$C_6$ alkanolamides of carboxylic $C_8$–$C_{22}$ alkyl ether acids are marketed, for example, by Henkel under the trademark COMPERLAN or by Chem Y under the trademark AMINOL;

the products of addition of ethylene oxide or of propylene oxide to partial esters of polyols and of fatty acids are marketed, for example, by BASF under the trademark CREMOPHOR or by Amerchol under the trademark GLUCAMATE;

polyoxyethylenated and/or polyoxypropylenated and/or polyglycerolated $C_{22}$–$C_{22}$ fatty alcohols are marketed, for example, by ICI under the trademark BRIJ, $C_{12}$–$C_{22}$ fatty esters of polyoxyethylene and/or of polyoxypropylene and/or of polyglycerol are marketed, for example, by ICI under the trademark MYRJ, polyethylene glycol and/or polypropylene glycol block polymers are marketed, for example, by ICI under the trademark SYNPERONIC.

The subject-matter of the invention is preferably a pressurized device as described above, characterized in that the aqueous composition B includes:

(a) 2 to 15% and, more preferably, from 3 to 12% by weight of at least one nonionic emulsifying surfactant; and (b) 2 to 15% by weight of at least one nonionic thickening surfactant.

The compositions of the present invention preferably include from 3 to 10% of at least one thickening surfactant as defined above. In practice the quantity of thickener employed is adapted to satisfy the abovementioned viscosity criterion. An excessive quantity of a compound of this type can result in a considerable thickening of the composition of the invention, which then becomes difficult to dispense as aerosol. Too small a quantity introduces the disadvantage of threatening the stability of the composition.

The compositions B advantageously additionally include at least one alkylpolyglucoside as nonionic surfactant. This alkylpolyglucoside preferably represents from 0.01 to 10% by weight of B.

The aqueous composition B preferably additionally includes at least one amphoteric surfactant, advantageously in quantities ranging from 0.01 to 15% by weight of B and, still more preferably, from 1 to 5% by weight of B.

According to a preferred composition, B includes:

1 to 25% by weight of at least one nonionic emulsifying surfactant, 1 to 30% by weight of at least one nonionic thickening surfactant, 0.01 to 10% by weight of at least one alkylpolyglucoside, 0.01 to 15% by weight of at least one amphoteric surfactant.

The compositions B may include up to approximately 98% of water. Water is usually intended to mean demineralized pure water. However, all or some of the water employed in the compositions B may optionally be selected from mineral or thermal waters. In general, a mineral water is suitable for consumption, which is not always the case with a thermal water. Each of these waters contains, inter alia, solubilized minerals and oligoelements. These waters are known to be employed for the purpose of specific treatment depending on the particular oligoelements and minerals which they contain, such as the hydration and desensitization of the skin or the treatment of certain types of dermatitis. Mineral or thermal waters will denote not only natural mineral or thermal waters but also natural mineral or thermal waters enriched in mineral constituents and/or in additional oligoelements, as well as mineral and/or oligoelemental aqueous solutions prepared from purified (demineralized or distilled) water.

A natural thermal or mineral water employed according to the invention may, for example, be selected from VITTEL water, VICHY basin waters, URIAGE water, ROCHE POSAY water, BOURBOULE water, ENGHIEN-LES-BAINS water, SAINT GERVAIS-LES-BAINS water, NERIS-LES-BAINS water, ALLEVAR-LES-BAINS water, DIGNE water, MAIZIERES water, NEYRAC-LES-BAINS water, LONS-LE-SAUNIER water, LES EAUX BONNES water, ROCHEFORT water, SAINT CHRISTAU water, FUMADES water, TERCIS-LES-BAINS water and AVENE water.

The cosmetic or dermatological compositions of the invention may additionally contain adjuvants which are usual in the fields concerned, such as, preservatives, antioxidants, perfumes, screening agents, colorants and hydrophilic or lipophilic agents.

The agents for the skin may be anti-aging agents, anti-wrinkle agents, hydrating or moisturizing agents, depigmenting agents, agents against free radicals (oxygen radical species), nutrient agents, protective agents, restructuring agents, firming agents, anti-acne agents, exfoliating agents, emollient agents or agents for treating skin diseases such as mycoses, dermatitis, psoriasis and the like. Depending on their nature, these agents are employed in the usual proportions, for example, from 0.01% to 10% by weight relative to the total weight of the composition.

The α-hydroxy acids (glycolic, lactic, malic, citric and similar acids) may be mentioned more particularly as anti-acne, anti-age, anti-wrinkle, hydrating and exfoliating agents.

Sulphites may be mentioned, for example, as antioxidants.

The following examples are given by way of illustration of the invention and are not of a limiting nature.

EXAMPLES

Compositions called B1 to B16 were prepared in accordance with the data given in Table I. These compositions were introduced into a pressurized bottle provided with a dispensing head, into which a pressurized gas was introduced. The whole was agitated so as to obtain a homogeneous mixture of the initial two phases. The devices were evaluated in Table I.

All the quantities are given as percentage by weight of active substance relative to the total weight of the composition.

The sodium N-cocoylamidoethyl,N-ethoxycarboxymethylglycinate amphoteric surfactant is marketed under the name of MIRANOL C2M by Rhône-Poulenc, PLANTAREN 2000, marketed by Henkel, is a mixture of alkyl ($C_8/C_{10}/C_{12}/C_{14}/C_{16}$ 29/37/23/9/2) polyglucosides, TWEEN 20 denotes the oxyethylenated (20 EO) sorbitan monolaurate (nonionic surfactant) marketed by ICI. With the exception of LUCAS water, the water employed in the examples was a demineralized water.

The viscosity of the aqueous compositions $B_1$ to $B_{16}$ in mPa s was evaluated and then these aqueous compositions were packaged in transparent pressurized bottles by introducing into these bottles 97% by weight of the composition and 3% by weight of isobutane. The transparency and the stability of these pressurized devices were subsequently measured after several months' storage at ambient temperature.

$T_5$: oxyethylenated methylglucoside dioleate (120 EO)

$T_6$: oxyethylenated (160 EO) sorbitan triisostearate $T_7$: polyglycerolated (3.5 moles) dodecanediol alcohol $T_8$: PEG (100 EO) monostearate $T_g$: block polymer of polyoxyethylene and of polyoxypropylene (EO/PO/EO 98/67/98)

$T_{10}$: oxyethylenated (200 EO) palm glyceride and oxyethylenated (70 EO) coprah glyceride (80/20)

$T_{11}$: oxyethylenated (60 EO) cetylstearyl ($C_{16}/C_{18}$) alcohol ether of myristyl glycol.

It is noted that all the compositions with the exception of $B_3$ were transparent and exhibited no halo, either at the time of their preparation or after several months' storage. Example $B_3$ does not form part of the invention.

TABLE 1

|  | $B_1$ | $B_2$ | $B_3$ | $B_4$ | $B_5$ | $B_6$ | $B_7$ | $B_8$ |
|---|---|---|---|---|---|---|---|---|
| Thickener | $T_1$/1% | $T_1$/0.75% | $T_2$/0.9% | $T_1$/1.3% | $T_1$/1% | $T_1$/1.5% | $T_1$/2% | $T_1$/1% |
|  | $T_2$/0.9% | $T_2$/0.9% | $T_{10}$/2.1% | T2/0.9% | $T_2$0.9% | $T_2$/0.9% | $T_2$/0.9% | $T_2$/0.9% |
|  | $T_{10}$/3.5% | $T_{10}$/3.5% | $T_{11}$/0.5% | $T_{10}$/2.1% | $T_{10}$/2.1% | $T_{10}$/2.1% | $T_{10}$/2.1% | $T_{10}$/2.1% |
| Tween 20 emulsifier | 4% | 5% | 6% | 10% | 11% | 6% | 6% | 6% |
| Miranol C2M | 1.9% | 1.9% | 1.9% | 1.9% | 1.9% | 1.9% | — | 3.8% |
| Plantareen 2000 | 2.5% | 2.5% | 2.5% | 2.5% | — | 2.5% | 2.65% | 2.65% |
| Glycerol | 4 | 4 | 0 | 4 | 4 | 4 | 4 | 4 |
| Citric acid | 2 | 2 | 2 | 2 | 2 | 2 | 2 | 2 |
| 2-Phenoxyethanol | 1 | 1 | 1 | 1 | 1 | 1 | 1 | 1 |
| Perfume | — | 1 | 0.8 | 0.8 | 0.8 | — | 0.6 | 0.6 |
| Lucas water | — | — | — | 5 | — | — | — | — |
| Water | q.s. 100 | q.s. 100 | q.s. 100 | q.s. 100 | q.s. 100 | q.s. 100 | q.s. 100 | q.s 100 |
| Viscosity | 66–70 | 90–96 | 16–22 | 50–51 | 14–20 | 88–94 | 72–78 | 36–40 |
| Transparency | + | + | 0 | + | + | + | + | + |
| Stability | 1 | 1 | 0 | 1 | 1 | 1 | 1 | 1 |

|  | $B_9$ | $B_{10}$ | $B_{11}$ | $B_{12}$ | $B_{13}$ | $B_{14}$ | $B_{15}$ | $B_{16}$ |
|---|---|---|---|---|---|---|---|---|
| Thickener | $T_5$/0.5% | $T_2$/0.9% | $T_7$/0.77% | $T_2$/0.9% | $T_2$/0.9% | $T_2$/0.9% | $T_2$/0.9% | $T_2$/1.8% |
|  | $T_2$/0.9% | $T_6$/0.5% | $T_2$/0.9% | $T_8$/0.5% | $T_9$/1% | $T_3$/1% | $T_4$/0.5% |  |
|  | $T_{10}$/2.1% | $T_{10}$/2.1% | $T_{10}$/2.1% | $T_{10}$/2.1% | $T_{10}$/2.1% | $T_{10}$/2.1% | $T_{10}$/2.1% | $T_{10}$/2.1% |
| Tween 20 | 6% | 6% | 6% | 6% | 6% | 6% | 6% | 6% |
| Miranol | 1.9% | 1.9% | 1.9% | 1.9% | 1.9% | 1.9% | 1.9% | 1.9% |
| Plantareen | 2.5% | 2.65% | 2.65% | 2.65% | 2.65% | 2.65% | 2.65% | 2.65% |
| Glycerol | — | — | — | — | — | — | — | — |
| Citric acid | 2% | 2% | 2% | 2% | 2% | 2% | 2% | 2% |
| 2-Phenoxyethanol | 1% | 1% | 1% | 1% | 1% | 1% | 1% | 1% |
| Perfume | 0.8% | 0.8% | 0.8% | 0.8% | 0.8% | 0.8% | 0.8% | 0.8% |
| Lucas water | — | — | — | — | — | — | — | — |
| Water | q.s. 100 | q.s. 100 | q.s. 100 | q.s. 100 | q.s. 100 | q.s. 100 | q.s. 100 | q.s 100 |
| Viscosity | 20–26 | 14–22 | 16–20 | 10–18 | 18–22 | 12–20 | 14–18 | 6–12 |
| Transparency | + | + | + | + | + | + | + | + |
| Stability | 1 | 1 | 1 | 1 | 1 | 1 | 1 | 1 |

The viscosity is given in mPa s. It was measured at 25° C. with the aid of a Brookfield viscometer in which the speed of the rotor module (module 1) was fixed at 5 revolutions/min.

the transparency is marked +, 0, or –:
  + meaning transparent, 0 meaning presence of a halo, – meaning turbidity
the stability is marked 0 or 1:
  1 meaning stable, 0 meaning unstable
The various thickeners are designated $T_1$ to $T_{10}$:
$T_1$: coprah acids monoethanolamide
$T_2$: castor oil
$T_3$: oxyethylenated oleyl alcohol (50 EO)
$T_4$: stearic acid amide ($C_{16}/C_{18}$ 30/70) (50 EO)

What is claimed is:

1. A pressurized device comprising:
(i) a pressurized bottle provided with a dispensing head; and
(ii) a single-phase transparent composition comprising:
  (A) 0.5 to 10% by weight of a propellant gas selected from the group consisting of hydrocarbon gases and fluorinated gases;
  (B) 90 to 99.5% by weight of an aqueous composition comprising a mixture of surfactants selected from nonionic surfactants and amphoteric surfactants; including (1) at least one nonionic emulsifying surfactant and (2) at least one nonionic thickening surfactant independently selected from (a) the $C_1$–$C_6$ alkanolamides of carboxylic $C_8$–$C_{22}$ alkyl ether acid;

(b) the addition products of 10 to 300 moles of ethylene oxide or of propylene oxide to partial esters of polyols containing 2 to 16 carbon atoms and of fatty acids containing 12 to 22 carbon atoms;

(c) poloxyethylenated $C_{12}$–$C_{22}$ fatty alcohols, polyoxypropylenated $C_{12}$–$C_{22}$ fatty alcohols, polyglycerolated $C_{12}$–$C_{22}$ fatty alcohols and mixtures thereof;

(d) $C_{12}$–$C_{22}$ fatty esters of polyoxyethylene, polyoxypropylene, polyglycerol, and mixtures thereof; and (e) polyethylene glycol block polymers polypropylene glycol block copolymers and mixtures thereof said device being suitable for dispensing a foam when the dispensing head is activated.

2. A device according to claim 1, wherein said pressurized bottle is transparent.

3. A device according to claim 1, wherein said single-phase transparent composition further comprises at least one adjuvant selected from preservatives, anti-oxidants, perfumes, screening agents, colorants, hydrophilic agents, and lipophilic agents.

4. A device according to claim 1, wherein said aqueous composition B comprises from 1 to 25% weight percent of said at least one nonionic emulsifying surfactant.

5. A device according to claim 1 wherein said aqueous composition B comprises from 1 to 30% of said at least one nonionic thickening surfactant.

6. A device according to claim 1, wherein said aqueous composition B has a Brookfield viscosity of from 5 to 200 mPa s.

7. A device according to claim 1 comprising from 1.5 to 4% by weight of said propellant gas relative to the total weight of said single-phase transparent composition.

8. A device according to claim 1, wherein said propellant gas is selected from hydrocarbon gases containing 2 to 6 carbon atoms.

9. A device according to claim 1, wherein said at least one nonionic emulsifying surfactant is selected from those having a hydrophiliclipophilic balance of from 12 to 18.

10. A device according to claim 9, wherein said at least one nonionic emulsifying surfactant is selected from the addition products of 1 to 200 moles of ethylene oxide or of propylene oxide to partial esters of polyols containing 2 to 16 carbon atoms and of fatty acids containing 12 to 22 carbon atoms.

11. A device according to claim 10, wherein said at least one nonionic emulsifying surfactant has a degree of esterification less than or equal to 2.

12. A device according to claim 3, wherein said single-phase transparent composition further comprises at least one antioxidant selected from sulphites.

13. A device according to claim 1, wherein said aqueous composition B comprises at least two of said thickening surfactants, each belonging to two different classes selected from said thickener classes (a) to (e).

14. A device according to claim 10, wherein said polyols are selected from glycol, glycerol, glucose, fructose, maltose, ribose, arabinose, xylose, lyxose, ribulose, xylulose, allose, altrose, mannose, gulose, galactose, sucrose and sorbitol.

15. A device according to claim 1, wherein said at least one nonionic thickening surfactant is selected from castor oil, monoethanolamides of carboxylic alkyl ($C_{13}$, $C_{15}$) ether acid with a degree of ethoxylation of 2 (2 EO), the monoethanolamide of carboxylic ether acid (50 EO), oxyethylenated (200 EO) tallow mono- and diglycerides, oxyethylenated (82 EO) tallow mono- and diglycerides, oxyethylenated (78 EO) copra mono- and diglycerides, stearic and hydroxystearic acid triglycerides (40 EO), polyethylene glycol monostearate (100 EO), poly-glycerolated (3.5 moles) dodecanediol alcohol, oxy-ethylenated (250 EO) 2-octyldodecanol, oxyethylenated (100 EO) stearyl alcohol, oxyethylenated (50 EO) oleyl alcohol, polyethylene glycol (50 EO) dioleate, oxyethylenated (200 EO) glycerol palmitate, oxyethylenated (160 EO) sorbitan triisostearate, oxyethylenated (200 EO) sorbitan triisostearate, polyethylene glycol (150 EO) stearate, oxyethylenated (120 EO) methylglucose dioleate, oxyethylenated (1 50 EO) pentaerythrityl tetrastearate, polyethylene glycol (55 EO) dioleate, polyethylene glycol (300 EO) undecylenate and polyethylene glycol (1 50 EO) distearate.

16. A device according to claim 1, wherein said at least one nonionic emulsifying surfactant is selected from oxyethylenated (7 EO) glycerol monoundecylenate, oxyethylenated (15 EO) glycerol monostearate, oxyethylenated (20 EO) glycerol monolaurate, oxyethylenated (20 EO) glycerol dilaurate, oxyethylenated (4 EO) diglycerol stearate, oxyethylenated (7 EO) glycerol cocoate, the pyrrolidonecarboxylate of oxyethylenated (250 EO) glycerol monoisostearate, oxyethylenated (20 EO) glycerol monostearate, oxyethylenated (30 EO) glycerol monostearate, oxyethylenated (4 EO) diglycerol stearate, oxyethylenated (30 EO) copra mono- and diglycerides, oxyethylenated (40 EO) sorbitan lanolate, oxyethylenated (20 EO) sorbitan monooleate, oxyethylenated (2 0 EO) sorbitan trioleate, oxyethylenated (20 EO) sorbitan monopalmitate, oxyethylenated (20 EO) sorbitan monostearate, oxyethylenated (20 EO) sorbitan monolaurate, oxyethylenated (20 EO) sorbitan undecylenate, oxyethylenated (18 EO) sorbitan undecylenate, oxyethylenated (6 EO) sorbitan hexastearate, oxyethylenated (44 EO) sorbitan monolaurate, oxyethylenated (30 EO) sorbitan tetraoleate, oxyethylenated (4 EO) sorbitan monostearate, oxyethylenated (40 EO) sorbitan oleate, oxyethylenated (4 EO) sorbitan monolaurate, oxyethylenated (10 EO) sorbitan monolaurate, oxyethylenated (40 EO) sorbitan tetraoleate, oxyethylenated (3 EO) butylglucoside cocoate, oxypropylenated (20 PO) methylglucoside distearate, oxyethylenated (20 EO) methylglucoside monolaurate, oxyethylenated (20 EO) methylglucose benzoate, oxyethylenated (1.4 EO) castor and sucrose triglyceride esters, oxyethylenated (2 EO) castor and sucrose triglyceride esters, oxyethylenated (20 EO) methylglucose sesquistearate, oxyethylenated (20 EO) methylglucose distearate, oxyethylenated (4 EO) butanediol monostearate, oxyethylenated (50 EO) polyethylene glycol monostearate, polyethylene glycol distearate, polyethylene glycol (8 EO) myristate, polyethylene glycol (8 EO) monostearate, polyethylene glycol (20 EO) monostearate, polyethylene glycol (6 EO) laurate, polyethylene glycol (8 EO) distearate, polyethylene glycol (8 EO) dilaurate, polyethylene glycol (8 EO) monooleate, tetraethylene glycol diheptanoate, polyethylene glycol (8 EO) dioleate, polypropylene glycol (26 EO) oleate, polyethylene glycol (30 EO) dipolyhydroxystearate (6 hydroxy), polyethylene glycol (40 EO) stearate and polyethylene glycol (8 EO) dilaurate.

17. A device according to claim 1, wherein said aqueous composition B comprises:

(a) 2 to 15% by weight of said at least one nonionic emulsifying surfactant, (b) 2 to 15% by weight of said at least one nonionic thickening surfactant.

18. A device according to claim 17, wherein said aqueous composition B comprises 3 to 12% by weight of said at least one nonionic emulsifying surfactant.

19. A device according to claim 1, wherein said aqueous composition B has a Brookfield viscosity of from 10 to 150 mPa s.

20. A device according to claim 17, wherein said aqueous composition B comprises from 3 to 6% by weight of said at least one nonionic thickening surfactant.

21. A device according to claim 1, wherein said aqueous composition B further comprises at least one alkylpolyglucoside.

22. A device according to claim 21, wherein said aqueous composition B comprises 0.01 to 15% by weight of said at least one alkylpolyglucoside.

23. A device according to claim 1, wherein said aqueous composition comprises at least one amphoteric surfactant.

24. A device according to claim 23, wherein said at least one amphoteric surfactant is present in said aqueous composition B in an amount ranging from 0.01 to 15% by weight.

25. A device according to claim 1, wherein said aqueous composition B comprises:

1 to 25% by weight of said at least one nonionic emulsifying surfactant;

1 to 30% by weight of said at least one nonionic thickening surfactant;

0.01 to 10% by weight of at least one alkylpolyglucoside; and 0.01 to 15% by weight of at least one amphoteric surfactant.

26. A device according to claim 1, wherein said single-phase transparent composition comprises mineral water or thermal water.

27. A device according to claim 1, wherein said single-phase transparent composition further comprises at least one α-hydroxy acid.

28. A process for cleansing or care of human skin comprising the step of applying to said skin a pressurized single-phase transparent composition comprising:

(A) 0.5 to 10% by weight of a propellant gas selected from the group consisting of hydrocarbon gases and fluorinated gases;

(B) 90 to 99.5% by weight of an aqueous composition comprising a mixture of surfactants selected from nonionic surfactants and amphoteric surfactants including (1) at least one nonionic emulsifying surfactant, and (2) at least one nonionic thickening surfactant selected from:

(a) the $C_1$–$C_6$ alkanolamides of carboxylic $C_8$–$C_{22}$ alkyl ether acid;

(b) the addition products of 10 to 300 moles of ethylene oxide or of propylene oxide to partial esters of polyols containing 2 to 16 carbon atoms and of fatty acids containing 12 to 22 carbon atoms;

(c) poloxyethylenated $C_{12}$–$C_{22}$ fatty alcohols, polyoxypropylenated $C_{12}$–$C_{22}$ fatty alcohols, polyglycerolated $C_{12}$–$C_{22}$ fatty alcohols and mixtures thereof;

(d) $C_{12}$–$C_{22}$ fatty esters of polyoxyethylene, polyoxypropylene, polyglycerol, and mixtures thereof; and (e) polyethylene glycol block polymers polypropylene glycol block copolymers and mixtures thereof.

* * * * *

UNITED STATES PATENT AND TRADEMARK OFFICE
CERTIFICATE OF CORRECTION

PATENT NO. : 5,888,478
DATED : March 30, 1999
INVENTOR(S) : Véronique Maurin

It is certified that error appears in the above-identified patent and that said Letters Patent is hereby corrected as shown below:

IN THE CLAIMS:

Claim 9, col. 9, line 44, "hydrophiliclipophilic" should read --hydrophilic-lipophilic--.

Claim 15, col. 10, lines 15 and 18, "(1 50 EO)" should read --(150 EO)--.

Signed and Sealed this

Twenty-fourth Day of August, 1999

Attest:

Q. TODD DICKINSON

Attesting Officer

Acting Commissioner of Patents and Trademarks